United States Patent [19]

Hähnle et al.

[11] Patent Number: 4,552,699
[45] Date of Patent: Nov. 12, 1985

[54] PROCESS FOR THE PREPARATION OF 3-ACYLAMINOANILINES

[75] Inventors: Reinhard Hähnle, Königstein/Taunus; Theodor Grewer, Bad Soden am Taunus, both of Fed. Rep. of Germany

[73] Assignee: Hoechst Aktiengesellschaft, Frankfurt, Fed. Rep. of Germany

[21] Appl. No.: 560,919

[22] Filed: Dec. 13, 1983

[30] Foreign Application Priority Data

Dec. 15, 1982 [DE] Fed. Rep. of Germany ....... 3246367

[51] Int. Cl.⁴ ........................................... C07C 102/04
[52] U.S. Cl. .................................. 260/404.5; 564/139; 564/141
[58] Field of Search ................. 260/404.5 R; 564/139, 564/141

[56] References Cited

U.S. PATENT DOCUMENTS 2,694,072 11/1954 von Glahn et al. ................. 564/141

OTHER PUBLICATIONS

Wagner, R. B., Zook, H. D., *Synthetic Organic Chemistry*, N.Y., John Wiley & Sons, Inc., 1953, QD 262.W24, p. 567.

*Primary Examiner*—Charles F. Warren
*Assistant Examiner*—Elizabeth A. Flaherty
*Attorney, Agent, or Firm*—Connolly and Hutz

[57] ABSTRACT

A process for the preparation of 3-acylaminoanilines of the general formula (1)

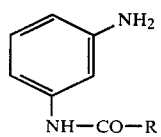

(1)

in which R denotes a branched or unbranched alkyl radical having 1–7 carbon atoms or the phenyl group, which can be substituted by 1–2 methyl groups or by 1–2 chlorine atoms, which comprises reacting a carboxylic acid of the general formula (2)

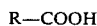

(2)

in which R has the meaning mentioned, with an excess of 1,3-diaminobenzene, and separating the reaction mixture by distillation.

5 Claims, No Drawings

PROCESS FOR THE PREPARATION OF 3-ACYLAMINOANILINES

It is known that 3-acylaminoanilines can be prepared by partial acylation of 1,3-diaminobenzenes. Thus, for example, a process for the preparation of compounds of the general formula

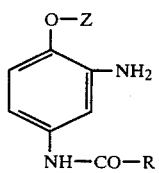

in which R and Z each denote an alkyl group, by partial acylation of the corresponding 1,3-diaminobenzene compounds is described in European Patent Specification No. 0,011,048. However, this process fails in the case of unsubstituted 3-acylaminoanilines because the possibility of partial acylation according to the known process is based on the markedly different reactivity of the two amino groups contained in the 2,4-diaminophenol ethers.

The process, described in German Offenlegungsschrift No. 2,455,212, for the monoacylation of a primary diamine which contains no sulfonic acid groups is based on the fact that, in a solution of the 1,3-diaminobenzene in hydrochloric acid, the monoprotonated compound of the formula

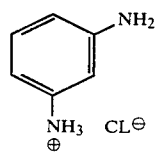

which can be acylated is still present in sufficient concentration, because the positive charge which is present makes second protonation difficult, while the monoacyl compound is virtually completely present as the hydrochloride of the formula

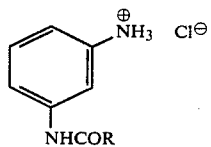

in which R denotes an alkyl group, which is not acylated to give the diacyl compound.

For acylation by the known processes mentioned, carbonyl chlorides or carboxylic anhydrides are employed, in excess in fact, and the reaction products obtained are isolated by salting out and filtering off, this producing heavily loaded effluent. The 3-acylaminoanilines are obtained by these processes as moist hydrochlorides, from which the free bases can be obtained by neutralization, effluent again being produced.

It has now been found that 3-acylaminoanilines of the general formula (1)

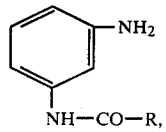

in which R denotes a branched or unbranched alkyl radical of 1–7 carbon atoms or the phenyl group, which can be substituted by 1–2 methyl groups or by 1–2 chlorine atoms, can be prepared without producing effluent and in good to very good yields by reacting a carboxylic acid of the general formula (2)

$$R-COOH \quad (2)$$

in which R has the meaning mentioned, with an excess of 1,3-diaminobenzene, and separating the reaction mixture by distillation. It is advantageous to allow the water being produced in the reaction to distil out during the reaction.

Suitable carboxylic acids are saturated fatty acids of 1 to 8 carbon atoms, as well as benzoic acid and its derivatives substituted in the benzene nucleus by 1 or 2 methyl groups or 1 or 2 chlorine atoms. In particular, acetic acid, propionic acid, butyric acid, isobutyric acid, valeric acid and benzoic acid are suitable.

The 1,3-diaminobenzene is employed in a two- to ten-fold, preferably three- to four-fold, molar excess compared with the carboxylic acid.

The reaction is carried out at 120°–240° C., preferably 155°–210° C.

It is advantageous to carry out the work-up by distillation of the resulting reaction mixture under reduced pressure at 0.1 to 50 torr.

The process is based on the fact that diacylation is statistically suppressed by the excess of 1,3-diaminobenzene, and on the fact that no undesired side reaction, for example no transacylation, takes place during workup by distillation, and this means that the reaction

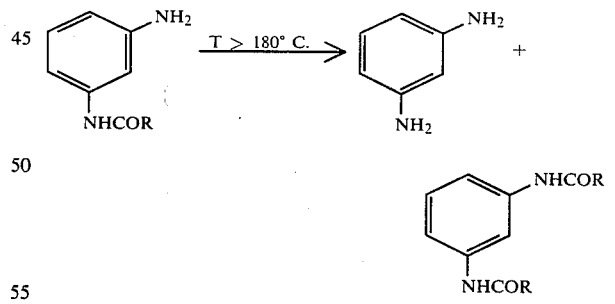

does not take place, which has to be regarded as being surprising, when the intense thermal stress during distillation is considered.

Assuming that every amino group present in the reaction mixture reacts with the same probability, the following equations are obtained for the composition of the reaction mixture:

$$A' = Ao - B + \frac{B^2}{4\,Ao}\;;\; C = B - \frac{B^2}{2\,Ao}\;;\; D = \frac{B^2}{4\,Ao}$$

In these equations:

Ao denotes the number of moles of diamine employed;
A denotes the number of moles of diamine in the reaction mixture;
B denotes the number of moles of carboxylic acid which have reacted;
C denotes the number of moles of monoacyl compound in the reaction mixture;
D denotes the number of moles of diacyl compound in the reaction mixture;

However, it emerged that an amino group of the 1,3-diaminobenzene reacts a factor of 1.19 more rapidly than does the amino group in 3-acylaminoaniline, which has to be regarded as being surprising.

Compared with the process described in German Offenlegungsschrift No. 2,455,212, which was mentioned earlier, the process according to the invention has the following advantages:

1. No effluent is produced.
2. The 3-acylaminoanilines do not result as hydrochlorides but as free, dry bases, and this is advantageous for further processing to produce commercial dyestuffs.
3. No acid chlorides or anhydrides are used, on the contrary, the acids themselves can be employed.

Considering strict regulations to protect the environment, the advantages mentioned outweigh the disadvantage of the greater amount of energy employed.

The 3-acylaminoanilines, of the general formula (1) mentioned, which can be obtained by the process are important intermediates in the preparation of azo dyestuffs.

EXAMPLE 1

756 g of molten 1,3-diaminobenzene (7.0 mole) and 222 g (3.0 mole) of propionic acid are initially introduced into a stirred flask which is provided with a 30 cm-long column, condenser and bend. The temperature in the interior of the flask is increased steadily to 170° C. within 1 hour, water distilling out. 170°–180° C. is then maintained for 1 hour. The reaction mixture is then separated by distillation into three fractions:
1st fraction (up to 100° C./1 torr) 72.5 g
2nd fraction (up to 160° C./1 torr) 517 g of 1,3-diaminobenzene
3rd fraction residue, 362.7 g of 3-propionylaminoaniline and 1,3-dipropionylaminobenzene.

The residue must be free of 1,3-diaminobenzene, and this is the case when 3-propionylaminoaniline appears at the thermometer at the head, and this can be demonstrated by chromatography.

The 1st fraction is titrated with 1N sodium hydroxide solution, then acidified and titrated with 1N sodium nitrite solution.

The 2nd fraction is weighed, and the residue is weighed and titrated with sodium nitrite solution.

Result:
1st fraction: 0.532 mole of propionic acid and 0.04 mole of 1,3-diaminobenzene.
2nd fraction: 4.787 mole of 1,3-diaminobenzene.
3rd fraction: 1.99 mole of 3-propionylaminoaniline and 0.165 mole of 1,3-dipropionylaminobenzene.
6.98 mole of the 1,3-diaminobenzene employed were recovered. 2.85 mole of the propionic acid employed were recovered.

The yield of 3-propionylaminoaniline, based on the 1,3-diaminobenzene consumed, is 91.5% of theory.

The 3-propionylaminoaniline obtained was processed to give the red commercial dyestuff of the formula

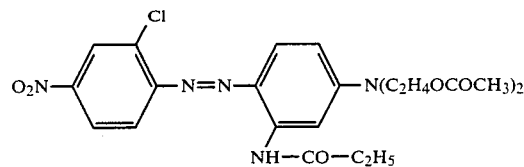

which was obtained satisfactorily.

EXAMPLE 2

756 g of 1,3-diaminobenzene (7.0 mole) and 120 g of acetic acid (2.0 mole) are initially introduced into a stirred flask provided with a 30 cm-long column, condenser and bend. The process is continued as described in Example 1. Working up by distillation produced:
1st fraction (100° C./1 torr) 50.5 g (0.395 mole) containing acetic acid.
2nd fraction (up to 160° C./1 torr) 579 g (5.36 mole) containing 1,3-diaminobenzene.
3rd fraction (residue) 238.5 g, including 1.56 mole (234 g) of 3-acetylaminoaniline and 0.023 mole (4.5 g) of 1,3-diacetylaminobenzene.

The yield, based on 1,3-diaminobenzene consumed, is 95.1% of theory.

EXAMPLE 3

756 g of 1,3-diaminobenzene (7.0 mole) and 264 g of butyric acid (3.0 mole) are initially introduced into a stirred flask provided with a 30 cm-long column, condenser and bend. The process is then carried out as described in Example 1. Working up by distillation produced:
1st fraction (up to 100° C./1 torr) containing 108 g (0.719 mole) of butyric acid and 0.05 mole of 1,3-diaminobenzene.
2nd fraction (up to 160° C./1 torr) 524 g of 1,3-diaminobenzene (4.852 mole)
3rd fraction (residue) 379 g, containing 1.954 mole of 3-butyrylaminoaniline (347.8 g) and 31.2 g of 1,3-dibutyrylaminobenzene (0.125 mole).

The yield, based on 1,3-diaminobenzene consumed, is 93% of theory.

EXAMPLE 4

When isobutyric acid is used in place of butyric acid, and the process is otherwise carried out as described in Example 3, then 1.465 mole of 3-isobutyrylaminoaniline are obtained, and this corresponds to a yield of 92% of theory, based on 1,3-diaminobenzene consumed.

EXAMPLE 5

756 g of 1,3-diaminobenzene (7.0 mole) and 306 g of n-valeric acid are initially introduced into the apparatus described in Example 1. The process is then carried out as described in Example 1, the following being obtained:
1st fraction: 164 g, containing 0.672 mole of valeric acid and 0.37 mole of 1,3-diaminobenzene
2nd fraction: 4.40 mole of 1,3-diaminobenzene
3rd fraction: (residue) 417 g, containing 2.00 mole of 3-valerylaminoaniline and 0.12 mole of 1,3-divalerylaminobenzene.

The yield, based on 1,3-diaminobenzene consumed, is 89.7% of theory.

EXAMPLE 6

756 g of 1,3-diaminobenzene (7.0 mole) and 148 g (2.0 mole) of propionic acid are initially introduced into the apparatus described in Example 1. The temperature is then rapidly increased to 120° C. and subsequently raised to 200° C. over the course of 5 hours. The gradual raising of the temperature is carried out so that the vapor passing through the column does not exceed a temperature of 102° C. at the head of the column. Working-up is then carried out as described in Example 1:

1st fraction: 48 g, containing 0.13 mole of propionic acid and 0.051 mole of 1,3-diaminobenzene.
2nd fraction: 553 g (5.12 mole) of 1,3-diaminobenzene.
3rd fraction: 298.5 g, containing 1.712 mole of 3-propionylaminoaniline (280.8 g) and 17.7 g of 1,3-dipropionylaminobenzene.

The yield of 3-propionylaminoaniline, based on 1,3-diaminobenzene consumed, is 93.6% of theory.

EXAMPLE 7

756 g of 1,3-diaminobenzene (7.0 mole) and 244 g of benzoic acid (2.0 mole) are heated at 200°–210° C. in the apparatus described in Example 1 for 4 hours. The residue obtained after distillation weighs 442 g and contains 1.945 mole (412 g) of 3-benzoylaminoaniline.

We claim:

1. A process for the preparation of a 3-acylaminoaniline of the formula (1)

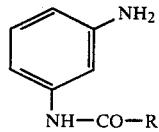

in which R denotes a branched or unbranched alkyl radical having 1–7 carbon atoms or a phenyl group, which can be substituted by 1–2 methyl groups or by 1–2 chlorine atoms, which comprises reacting a carboxylic acid of the formula (2)

in which R has the meaning mentioned, with an excess of 1,3-diaminobenzene, and separating the reaction mixture by distillation.

2. The process as claimed in claim 1, wherein the 1,3-diaminobenzene is employed in a two- to ten-fold molar excess.

3. The process as claimed in claim 1, wherein the reaction is carried out at 120° to 240° C.

4. The process as claimed in claim 1, wherein the water being produced in the reaction is allowed to distil out during the reaction.

5. The process as claimed in claim 1, wherein distillation under reduced pressure of 0.1 to 50 torr is carried out after the reaction.

* * * * *